(12) United States Patent
Hsiung et al.

(10) Patent No.: US 7,348,783 B1
(45) Date of Patent: Mar. 25, 2008

(54) MULTI-FUNCTIONAL PH METER AND FABRICATION THEREOF

(75) Inventors: Shen-Kan Hsiung, Tao-Yuan (TW);
Jung-Chuan Chou, Tao-Yuan (TW);
Tai-Ping Sun, Tao-Yuan (TW);
Nien-Hsuan Chou, Tao-Yuan (TW);
Gin-Chou Yang, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 0 days.

(21) Appl. No.: 11/465,776

(22) Filed: Aug. 18, 2006

(51) Int. Cl.
*G01N 27/00* (2006.01)
(52) U.S. Cl. ...................................... 324/438
(58) Field of Classification Search ................. 324/438
See application file for complete search history.

(56) References Cited

U.S. PATENT DOCUMENTS

| 5,814,280 | A | * | 9/1998 | Tomita et al. | ........... 422/82.01 |
| 2003/0132755 | A1 | * | 7/2003 | Feng et al. | ................. 324/438 |
| 2005/0147741 | A1 | * | 7/2005 | Hsiung et al. | ............. 427/97.1 |
| 2007/0071648 | A1 | * | 3/2007 | Busch et al. | ............. 422/82.05 |

* cited by examiner

*Primary Examiner*—Vincent Q. Nguyen
(74) *Attorney, Agent, or Firm*—WPAT, P.C.; Justin I. King

(57) ABSTRACT

A multi-functional PH meter and the fabrication thereof are disclosed. The multi-functional pH meter immediately displays the measurement result on a liquid crystal display and saves in a compact flash card so as to provide portable functionality. In addition, the multi-functional pH meter has data communication functionality with a computer. Finally, the drift and hysteresis software calibration technique is applied. Thus, this method can increase ion detection accuracy and system reliability. The multi-functional pH meter includes a sensor unit, an analog signal processing unit, a microprocessor unit, the liquid crystal display unit, the compact flash card unit and a data transmission unit.

17 Claims, 15 Drawing Sheets

| Measurement method / Buffer solution | Commercialized pH meter | Portable multi-functional pH meter ||| Error(%) |
|---|---|---|---|---|---|
| | | LCD | USB、UART | Compact flash card | |
| 2 | 2.07 | 2.15 | 2.15 | 2.15 | 4 |
| 4 | 4.07 | 4.23 | 4.23 | 4.23 | 4 |
| 6 | 6.11 | 6.26 | 6.26 | 6.26 | 2 |
| 8 | 7.53 | 7.35 | 7.35 | 7.35 | 2 |
| 10 | 9.80 | 9.55 | 9.55 | 9.55 | 3 |
| 12 | 11.66 | 11.39 | 11.39 | 11.39 | 2 |

Table.1

| | |
|---|---|
| Power source | 9V battery |
| Sensing electrode | tin dioxide/ indium tin oxide/glass separate structure extended gate field effect transistor |
| Reference electrode | Silver/silver chloride |
| Average sensitivity | 59mV/pH |
| microprocessor | PIC18F452 |
| Measurement range | pH2~pH12 |
| Resolution | 0.01pH |
| Calibration method | Two-point calibration (pH4, pH7) |
| Display part | LCD |
| | Compact flash card (capacity:256 MB) |
| Data transmission part (send to computer) | USB and UART |
| | Card reader |

Table.2

MULTI-FUNCTIONAL PH METER AND FABRICATION THEREOF

BACKGROUND OF THE INVENTION

1. Field of the Invention

The present invention is generally related to a multi-functional pH meter and fabrication thereof, and more particularly to a multi-functional pH meter and fabrication thereof by integrating semiconductor processes and embedded system technology.

2. Description of the Prior Art

Ion sensitive field effect transistors (ISFETs) are micro sensing devices appeared in 70s and quickly developed. For only 30 years till now, there are more than 600 research papers and 150 other related papers, such as enzyme field effect transistors (EnFETs) and immuno field effect transistors (IMFETs) (P. Bergveld, "Thirty years of ISFETOLOGY: What happened in the past 30 years and what may happen in the next 30 years", Sensors and Actuators B, Vol. 88, pp. 1-20, 2003.). In addition, ion sensitive field effect transistors can be used to measure pH values and ion concentrations, such as $Na^+$, $K^+$, $Cl^-$, $NH_4^+$, $Ca^{2+}$, in stead of fragile glass electrodes (Miao Yuqing, Guan Jianguo, and Chen Jianrong, "Ion sensitive field effect transducer-based biosensors", Biotechnology Advances, Vol. 21, pp. 527-534, 2003.). The idea was first introduced by P. Bergveld. By using a metal oxide semiconductor field effect transistor (MOSFET) without a gate electrode, a device with a $SiO_2$ layer is placed in aqueous solution together with a reference electrode. The electric current passing the device changes with the hydrogen-ion concentration, whose response is similar to that of a glass electrode. Thus, it has the acid-base sensing characteristic (Chen Jian-pin, Lee Yang-li, Kao Hung, "Ion sensitive field effect transistors and applications thereof", Analytical Chemistry, Vol. 23, No. 7, pp. 842-849, 1995; Wu Shih-hsiang, Yu Chun, Wang Kuei-hua, "Measurement by chemical sensors", Sensor technology, No. 3, pp. 57-62, 1990).

Some ISFET sensing devices have been commercialized, such as ISFET pH meters made by Arrow Scientific, Deltatrak, and Metropolis. However, it has problems of stability and lifetime, for example drift phenomena and hysteresis effect. The present invention discloses another type of ISFETs, an extended gate field effect transistor (EGFET). The field effect transistor (FET) is isolated from the chemical measurement environment. The chemical sensing film is deposited on one end of the signal wire extended from the area of the gate electrode. The portions of the electric effect and the chemical effect are packaged separately. Therefore, compared to conventional ISFETs, EGFETs are easy in packaging and storage and have better stability (Liao Han-chou, "Novel calibration and compensation technique of circuit for biosensors", June, 2004, Department of electrical engineering, Chung Yuan Christian University, Master dissertation, pp. 11-29).

Recently, there are many researches in characteristics of the extended gate ion sensitive field effect transistors, such as device design (Li Te Yin, Jung Chuan Chou, Wen Yaw Chung, Tai Ping Sun, and Shen Kan Hsiung, "Separate structure extended gate $H^+$-ion sensitive filed effect transistor on a glass substrate", Sensors and Actuators B, Vol. 71, 106-111, 2000; Li Te Yin, Jung Chuan Chou, Wen Yaw Chung, Tai Ping Sun, and Shen Kan Hsiung, "Study of indium tin oxide thin film for separative extended gate ISFET", Materials Chemistry and Physics, Vol. 70, pp. 12-16, 2001; Li Te Yin, Jung Chuan Chou, Wen Yaw Chung, Tai Ping Sun, Kuang Pin Hsiung, and Shen Kan Hsiung, "Study on glucose ENFET doped with $MnO_2$ powder", Sensors and Actuators B, Vol. 76, pp. 187-192, 2001; Yin Li-Te, "Study of Biosensors Based on an Ion Sensitive Field Effect Transistor", June, 2001, Department of biomedical engineering, Chung Yuan Christian University, Ph. D. dissertation, pp. 76-108.), characteristic analysis (Jia Yong-Long, "Study of the extended gate field effect transistor (EGFET) and signal processing IC using the CMOS technology", June, 2001, Department of electrical engineering, Chung Yuan Christian University, Ph. D. dissertation, pp. 36-44; Chen Jia-Chi, "Study of the disposable urea sensor and the pre-amplifier", June, 2002, Department of biomedical engineering, Chung Yuan Christian University, Master dissertation, pp. 51-80; Jia Chyi Chen, Jung Chuan Chou, Tai Ping Sun, and Shen Kan Hsiung, "Portable urea biosensor based on the extended-gate field effect transistor", Sensors and Actuators B, Vol. 91, pp. 180-186, 2003; Chung We Pan, Jung Chuan Chou, I Kone Kao, Tai Ping Sun, and Shen Kan Hsiung, "Using polypyrrole as the contrast pH detector to fabricate a whole solid-state pH sensing device", IEEE Sensors Journal, Vol. 3, pp. 164-170, 2003; Jui Fu Cheng, Jung Chuan Chou, Tai Ping Sun, and Shen Kan Hsiung, "Study on the chloride ion selective electrode based on the $SnO_2$/ITO glass", Proceedings of The 2003 Electron Devices and Materials Symposium (EDMS), National Taiwan Ocean University, Keelung, Taiwan, R.O.C., pp. 557-560, 2003; Jui Fu Cheng, Jung Chuan Chou, Tai Ping Sun, and Shen Kan Hsiung, "Study on the chloride ion selective electrode based on the $SnO_2$/ITO glass and double-layer sensor structure", Proceedings of The 10th International Meeting on Chemical Sensors, Tsukuba International Congress Center, Tsukuba, Japan, pp. 720-721, 2004.), characteristics of drift phenomena and hysteresis effect (Liao Han-chou, "Novel calibration and compensation technique of circuit for biosensors", Master dissertation, Department of electrical engineering, Chung Yuan Christian University, pp. 11-29, June, 2004; Chu Neng Tsai, Jung Chuan Chou, Tai Ping Sun, and Shen Kan Hsiung, "Study on the hysteresis of the metal oxide pH electrode", Proceedings of The 10th International Meeting on Chemical Sensors, Tsukuba International Congress Center, Tsukuba, Japan, pp. 586-587, 2004; Chu Neng Tsai, Jung Chuan Chou, Tai Ping Sun, and Shen Kan Hsiung, "Study on the sensing characteristics and hysteresis effect of the tin oxide pH electrode", *Sensors and Actuators B*, Vol. 108, pp. 877-882, 2005.).

SUMMARY OF THE INVENTION

Compared to the above described prior arts, the present invention provides a multi-functional pH meter by integrating semiconductor processes and embedded system technology. An acid-base sensing electrode with a tin dioxide/indium tin oxide/glass separate structure together with embedded system technology is used to fabricate the multi-functional pH meter.

The multi-functional pH meter according to the present invention immediately displays the measurement result on a liquid crystal display and saves in a compact flash card so as to have portable functionality. In addition, the multi-functional pH meter has data communication functionality with a computer. Finally, the drift and hysteresis software calibration technique is applied. Thus, this method can increase ion detection accuracy and system reliability. The device can be applied in pH value measurement. If other polymer selection substance is used, other type of ions can also be detected and applicability is also increased. It can also increase accuracy, applicability, and industrial applications in clinics, bio-signals, and environmental detection. Because the fabrication method requires only simple equipments, is also low in cost, and can be massively produced, the multi-functional pH meter according to the present invention has very high applicability in pH value measurement.

Figure 1:
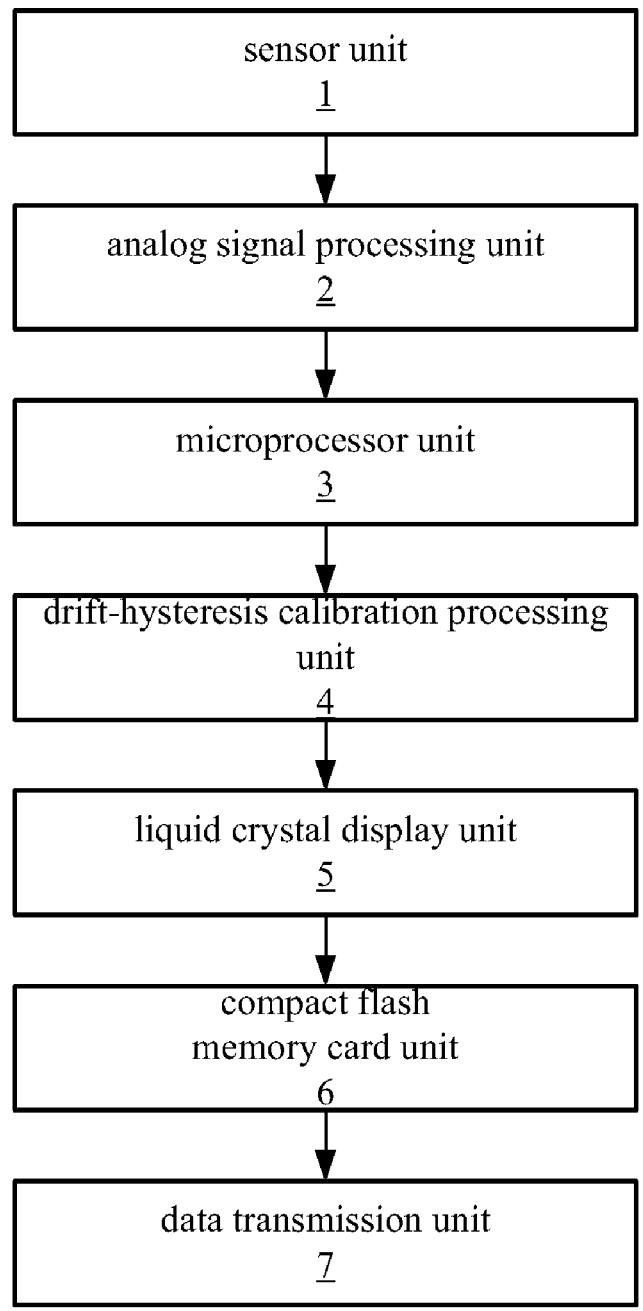
FIG. 1 is a design flow chart for the multi-functional pH meter in a preferred example according to the present invention.

Table 1 shows measurement results in various buffer solutions by the multi-functional pH meter in a preferred example according to the present invention.

Table 2 shows the specification of the multi-functional pH meter in a preferred example according to the present invention.

DESCRIPTION OF THE PREFERRED EMBODIMENTS

Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims. In order to have clear description of the invention and better understanding for those who are skilled in the art, some part of the figures is not drawn in proportion, in which the size of some part has been exaggerated. Besides, some of irrelevant part is not shown for simplicity.

In a preferred example of the present invention, fabricating a separate structure extended gate ion selective sensor includes the following steps:

An indium tin oxide film (ITO film) is formed on a substrate. In a preferred example of the present invention, the thickness of the indium tin oxide film is about 230 Å, but is not limited. The substrate is an insulation substrate, such as ceramic substrate, glass substrate. Glass substrate is preferred.

The glass substrate with the ITO film is placed in a solution, especially in methanol solution and deionized water, and oscillated by an ultrasonic oscillator. A preferred oscillation period is about 15 minutes each in the methanol solution and deionized water. It is not limited to 15 minutes.

The process for fabricating a sensing film comprises depositing a tin dioxide ($SnO_2$) film by physical vapor deposition method. A RF (radio frequency) sputtering method is preferred and the sputtering target is tin dioxide. Preferred material for the sensing film is tin dioxide, but is not limited to tin dioxide. Mixture gas is then flowing into the reaction chamber and the substrate is maintained at a constant temperature. Preferred mixture gas is mixture of argon and oxygen gas. The temperature of the substrate is preferably about 150° C. for depositing a tin dioxide ($SnO_2$) film, the deposition pressure is preferably about 20 mTorr, the RF power is preferably about 50 W, the thickness of the film is preferably about 2000 Å, and the mixing ratio of argon and oxygen is preferably 4:1.

Following that, a conductive wire is formed and packaging a sensing electrode is carried out. The conductive wire is preferably a silver wire. The conductive wire is adhered to the tin dioxide film via silver paste. The packaging material is preferably epoxy resin but can be other suitable material. Preferably, the epoxy resin sensing widow has an area of 3×3 $mm^2$.

A glass electrode is formed as a reference electrode to provide stable reference potential. The glass electrode is preferably a silver/silver chloride glass electrode but can be other suitable electrode.

Fabricating a sensing system according to the present invention comprises the following steps:

An amplifier is used as a front-end processing circuit and then filtering low-frequency noise is carried out. Considering interference of the low-frequency noise, a $2^{nd}$ order Butterworth filter is used to filter out low-frequency noise. The signal is sent to a level adjusting circuit for adjusting the potential level and then an output signal (output signal of step 1) is outputted for next step.

The output signal of step 1 is used as an input signal and transmitted to a PIC18F452 single chip microprocessor, using an embedded system as the core. After processing by the built-in 10-bit progressive A/D converter, a two-point (pH4, pH7) calibration procedure can be carried out and a quantized absolute pH value in the measurement range is calculated. The numerical value in each measurement interval is complete.

The sensor is placed in an unknown solution. Software calibration is carried out to improve the problems of hysteresis effect and drift phenomena in the sensor unit. Following that, the two-point (pH4, pH7) calibration procedure is performed to eliminate the error so as to provide more accurate sensing signal. Finally, the pH value measurement result is displayed on a liquid crystal display (LCD) immediately and saved in a memory card, such as a compact flash card (CF card). In a readout procedure from a CF card, data can be read to a computer via a card reader. In addition, the device according to the present invention can transmit the measurement result to a personal computer or a laptop computer via the transmission interface, such as universal serial bus (USB) and universal asynchronous receiver/transmitter (UART) interfaces, so as to enhance the flexibility of the system. By the above described method, the pH value of the unknown solution is informed to the user.

FIG. 1 is a design flow chart for the multi-functional pH meter in a preferred example according to the present invention. A sensor unit 1 is a transducer for measuring an unknown solution. An analog signal processing unit 2 is used as the circuit for processing the sensing signal. A microprocessor unit 3 is used for converting analog/digital signals and processing digital signals, comprising a drift-hysteresis calibration processing unit 4, a liquid crystal display unit 5, a compact flash memory card unit 6, and a data transmission unit 7, in the firmware portions.

Figure 2:
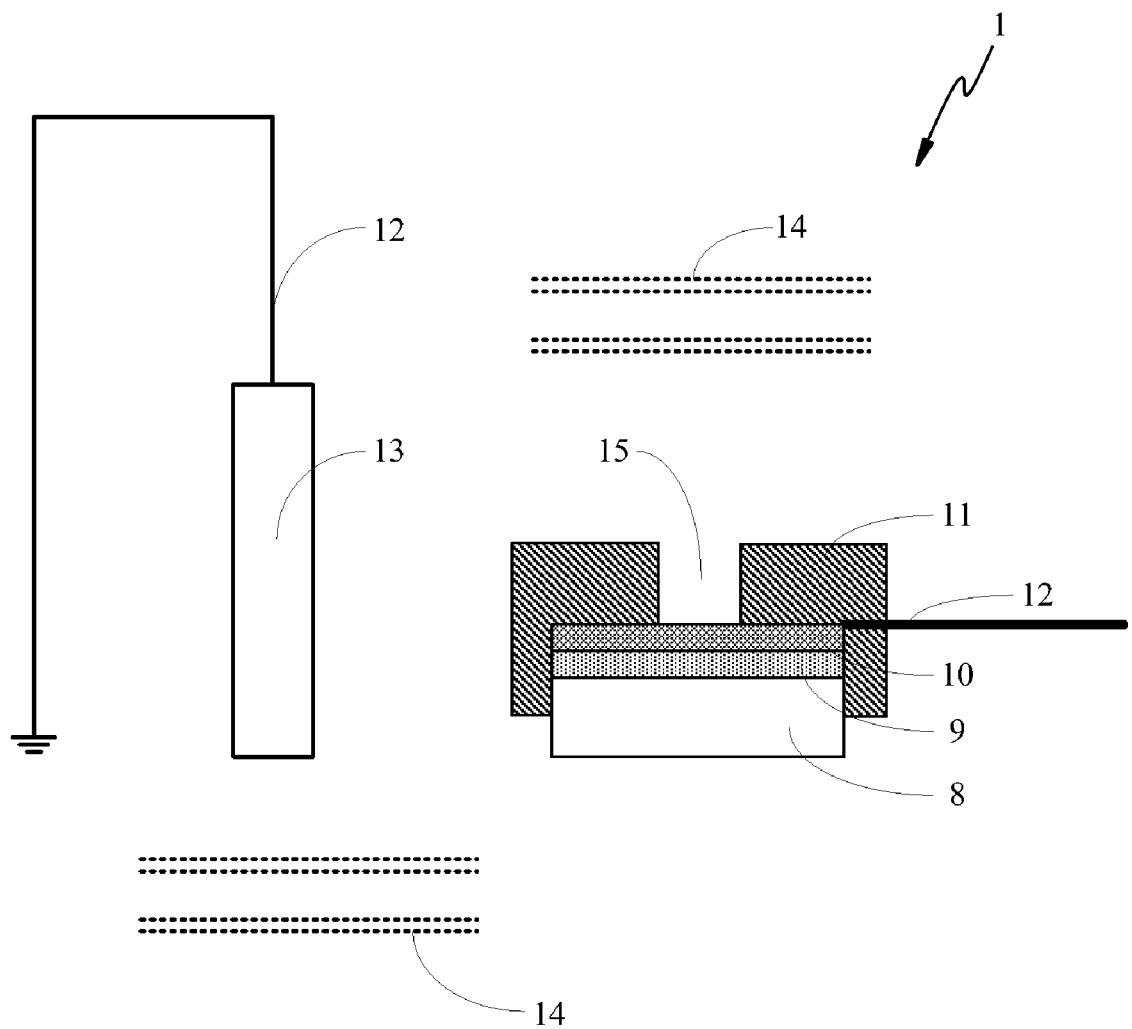
FIG. 2 is a structure schematic diagram for the multi-functional pH meter in a preferred example according to the present invention.

FIG. 2 is a structure schematic diagram for the pH sensor unit 1 using a tin dioxide sensing electrode in a preferred example according to the present invention. This sensor is easy to be fabricated and packaged. Thus, the cost is reduced and can be a disposable sensor. The sensor unit 1 in a preferred example according to the present invention, as shown in FIG. 2, comprises: a substrate 8, preferably a glass substrate; an indium tin oxide film 9 formed on the substrate 8; a tin dioxide film 10 formed on the indium tin oxide film 9 and connected to a conductive wire 12. A package material 11 covers the tin dioxide film 10, the indium tin oxide film 9, and a portion of the substrate 8 and has a sensing window 15 to expose a portion of the tin dioxide film 10. The package material 11 is preferably epoxy resin. An electrode 13 is connected to the conductive wire 12. The electrode 13 is preferably a silver/silver chloride electrode. This example uses tin dioxide/indium tin oxide/glass substrate as the basic structure and uses a silver/silver chloride electrode to provide stable reference potential so as to measure the reaction potential of the sensor unit placed in an unknown solution 14.

Figure 3:
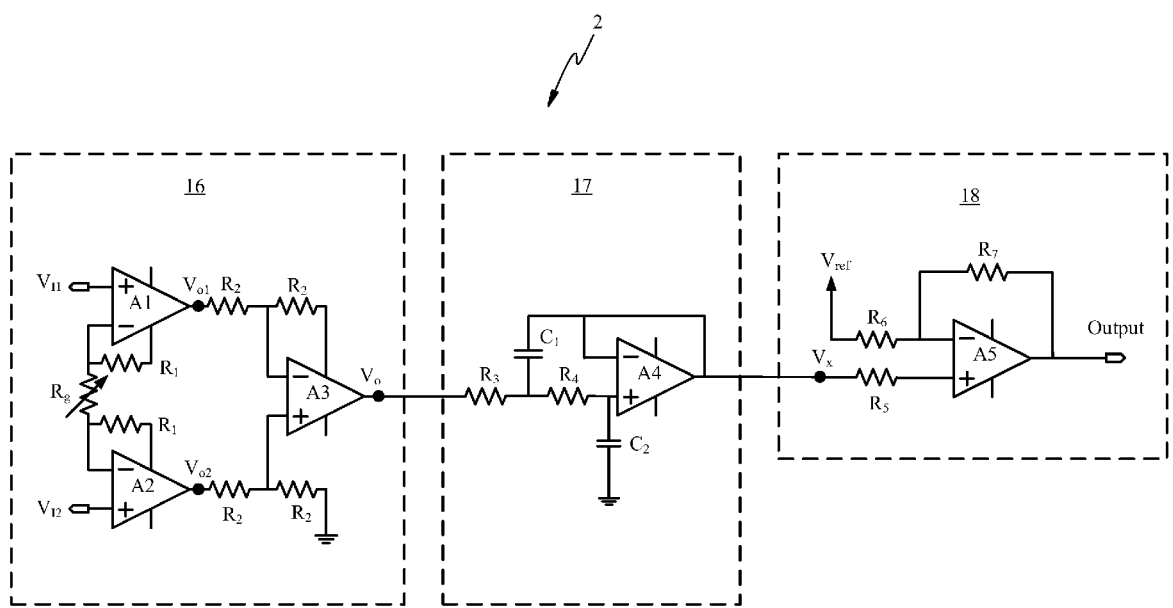
FIG. 3 is a circuit diagram of the analog signal processing unit in a preferred example according to the present invention.

FIG. 3 is a circuit diagram of the analog signal processing unit 2 in a preferred example according to the present invention. The analog signal processing unit 2 comprises an amplifier used as a primary processing circuit for a sensing signal to increase the signal-to-noise ratio of the sensing signal; a low pass filter for filtering out low frequency noises and suppressing the interference of the 60 Hz AC mains frequency to the sensing signal; and, a level adjusting circuit for adjusting the potential level of the processed sensing signal to fit the input range and specification of an analog/digital converter. The analog signal processing unit 2 gathers an appropriate signal according to the basic characteristic of the sensor unit and thereby uses an amplifier 16 as the front-end processing circuit for a sensing signal to increase the signal-to-noise ratio of the sensing signal. In order to eliminate interference of the low-frequency noise, a $2^{nd}$ order Butterworth filter 17 is used to filter out low-frequency noise. A level adjusting circuit 18 adjusts the potential level of the processed sensing signal transmitted from the amplifier 16. Thus, a stable sensing signal is obtained and thereby sent to a microprocessor unit (not shown). The usable IC serial number for the amplifier 16 comprises Model INA118. The usable IC serial number for the $2^{nd}$ order Butterworth filter 17 comprises Model LM324. The usable IC serial number for the level adjusting circuit 18 comprises Model LM324. The usable IC serial number for the microprocessor unit comprises PIC18F452.

Figure 4:
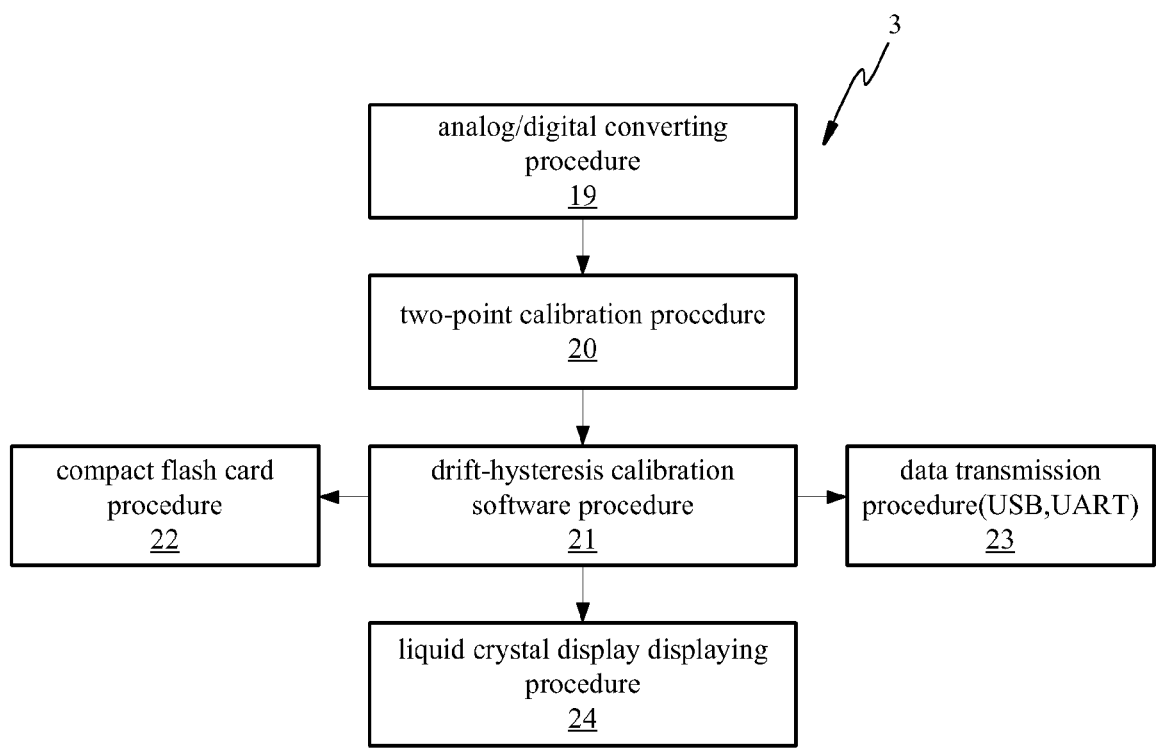
FIG. 4 is a process flow chart of the microprocessor unit in a preferred example according to the present invention.

FIG. 4 is a process flow chart of the microprocessor unit 3 in a preferred example according to the present invention. While receiving the signal transmitted from the analog signal processing unit 2, a 10-bit analog/digital converter built in the single chip microprocessor unit quantizes the analog signal, i.e. an analog/digital converting procedure 19 is carried out. After a two-point calibration procedure 20 is carried out, the pH value of the unknown solution is thus calculated. After processed by a drift-hysteresis calibration software procedure 21, the pH value of the unknown solution is immediately displayed on a liquid crystal display, i.e. a displaying procedure or liquid crystal display displaying procedure 24. The pH value is also simultaneously saved in a compact flash card, i.e. a memory storing procedure or compact flash card procedure 22. In a readout procedure from a CF card, data can be read to a computer via a card reader. In addition, the device according to the present invention can transmit the measurement result to a personal computer or a laptop computer via the transmission interface, such as universal serial bus (USB) and universal asynchronous receiver/transmitter (UART) interfaces, so as to enhance the flexibility of the system. By the above described method, the pH value of the unknown solution is informed to the user, i.e. data transmission procedure 23. The microprocessor unit comprises a firmware of analog/digital converting procedure for controlling 10-bit analog/digital converter built in the microprocessor unit, comprising controls of sampling rate, channel selection, and reference potential; a firmware of two-point calibration procedure for completing the two-point calibration procedure; and, a firmware of drift and hysteresis calibration procedure for calibrating drift and hysteresis.

Figure 5:
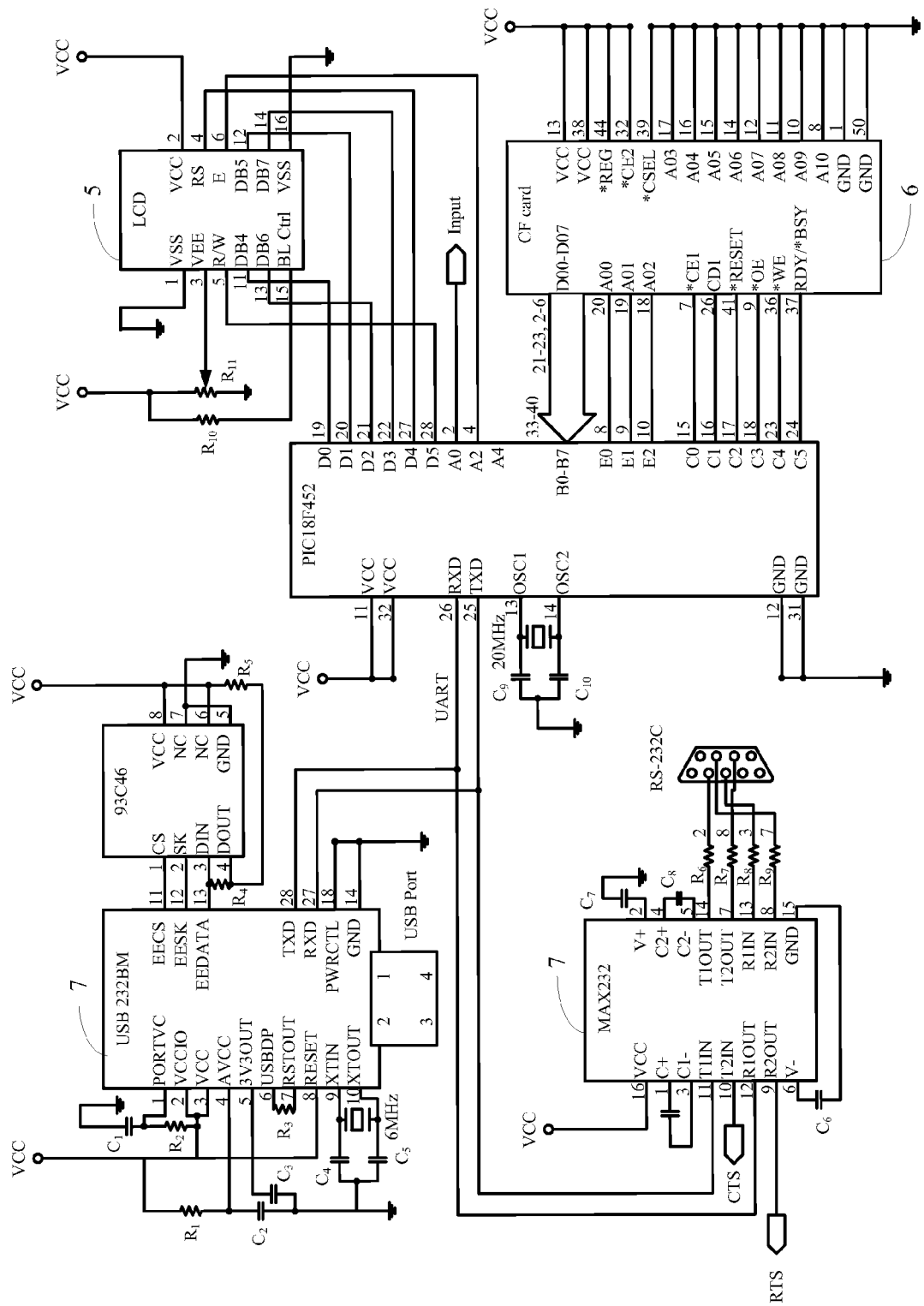
FIG. 5 is a peripheral circuit diagram of the microprocessor unit in a preferred example according to the present invention.

FIG. 5 is a peripheral circuit diagram of the microprocessor unit 3 in a preferred example according to the present invention, comprising pinout diagrams for a liquid crystal display unit 5, a compact flash card unit 6, universal serial bus (USB) and universal asynchronous receiver/transmitter (UART) interfaces of a data transmission unit 7.

Figure 6:
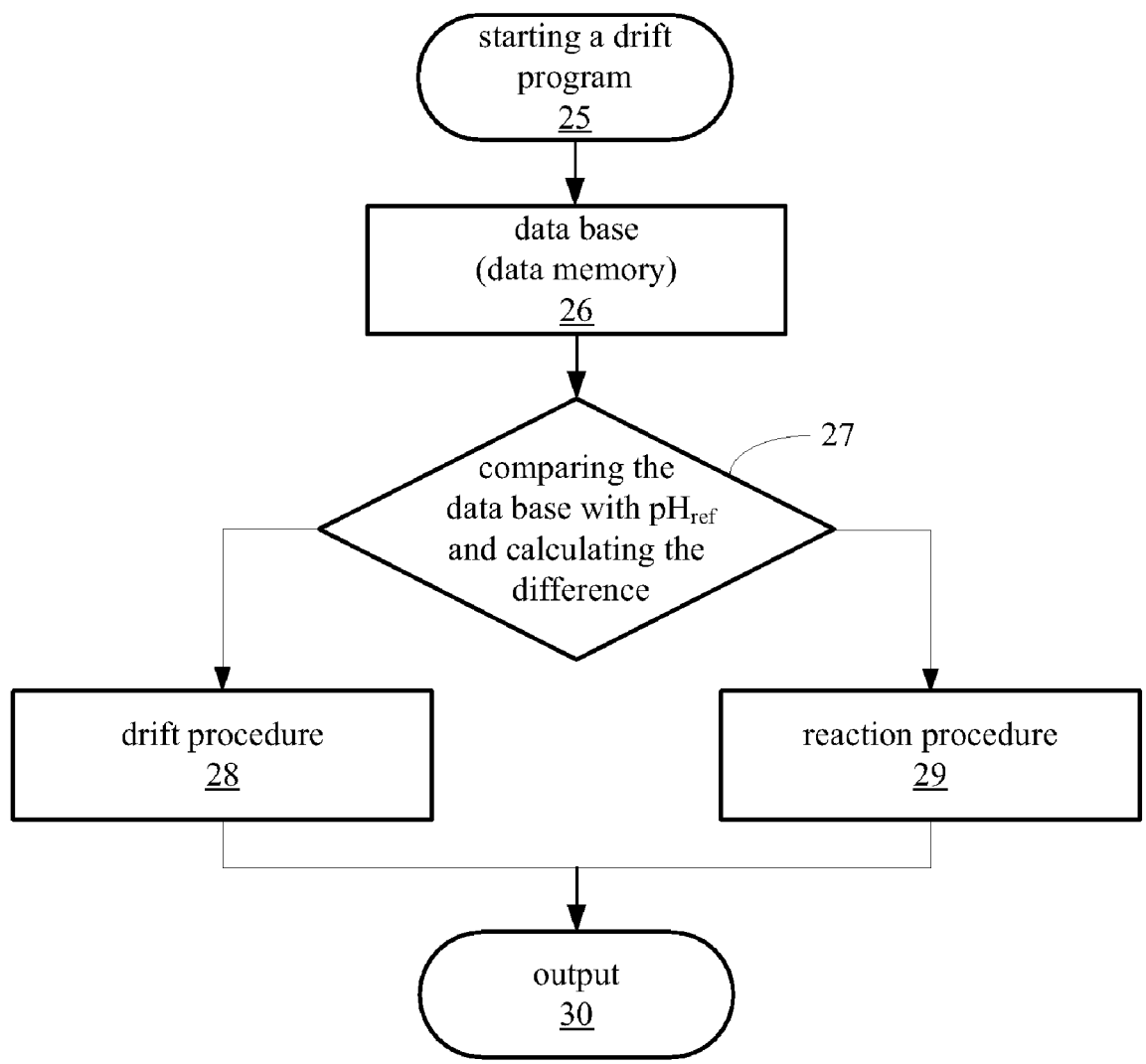
FIG. 6 shows a program flow chart of the drift calibration procedure in a preferred example according to the present invention.

FIG. 6 shows a program flow chart of the drift calibration procedure, comprising:

starting a drift program 25 (using a PIC18F452 microprocessor as a processing core);

recording every measurement value in a data memory as a data base 26;

comparing the data base with the reference pH value ($pH_{ref}$) and calculating the difference 27 for each measurement;

determining if the difference is caused by drift phenomena and then carrying out a drift procedure 28, or if the difference is caused by variation in the unknown solution and then carrying out an appropriate calibration, i.e. processing with a reaction procedure 29;

outputting the result from the drift calibration procedure, i.e. output 30.

Figure 7:
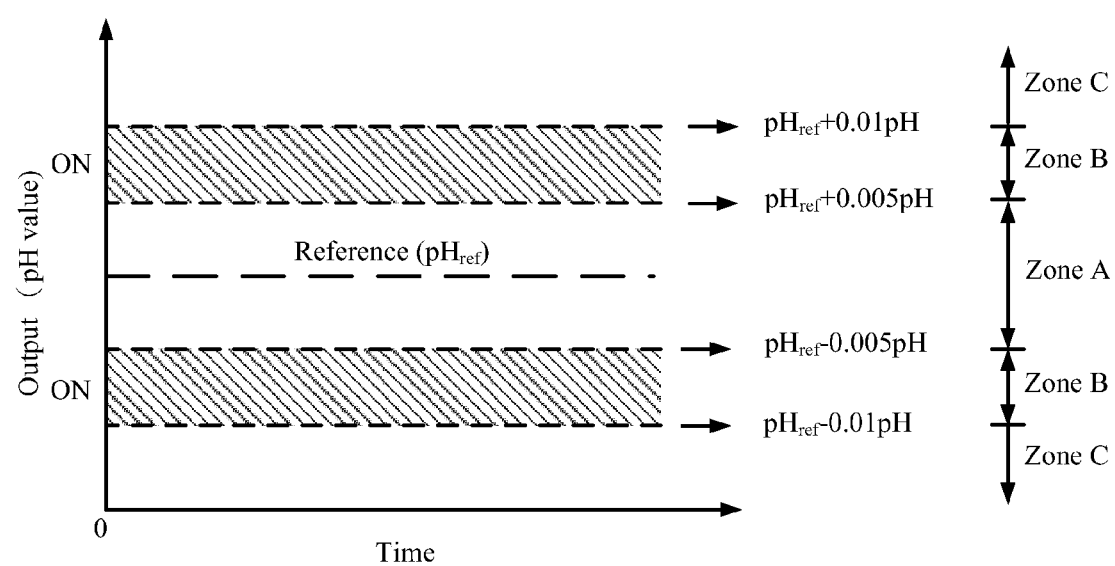
FIG. 7 is a schematic diagram illustrating the drift calibration principle in a preferred example according to the present invention.

FIG. 7 is a schematic diagram illustrating the drift calibration principle in a preferred example according to the present invention, shown in the following:

Working zone→Zone A: normal zone; Zone B: calibration zone; Zone C: Reaction zone.

Zone A: if the output pH value is between ($pH_{ref}$−0.005) (pH) and ($pH_{ref}$+0.005) (pH), the calibration procedure is not executed.

Zone B: if the output pH value is smaller than ($pH_{ref}$−0.005) (pH) or greater than ($pH_{ref}$+0.005) (pH), the calibration procedure is executed.

Zone C: if the output pH value is smaller than ($pH_{ref}$−0.01) (pH) or greater than ($pH_{ref}$+0.01) (pH), the unknown solution is varied.

Figure 8:
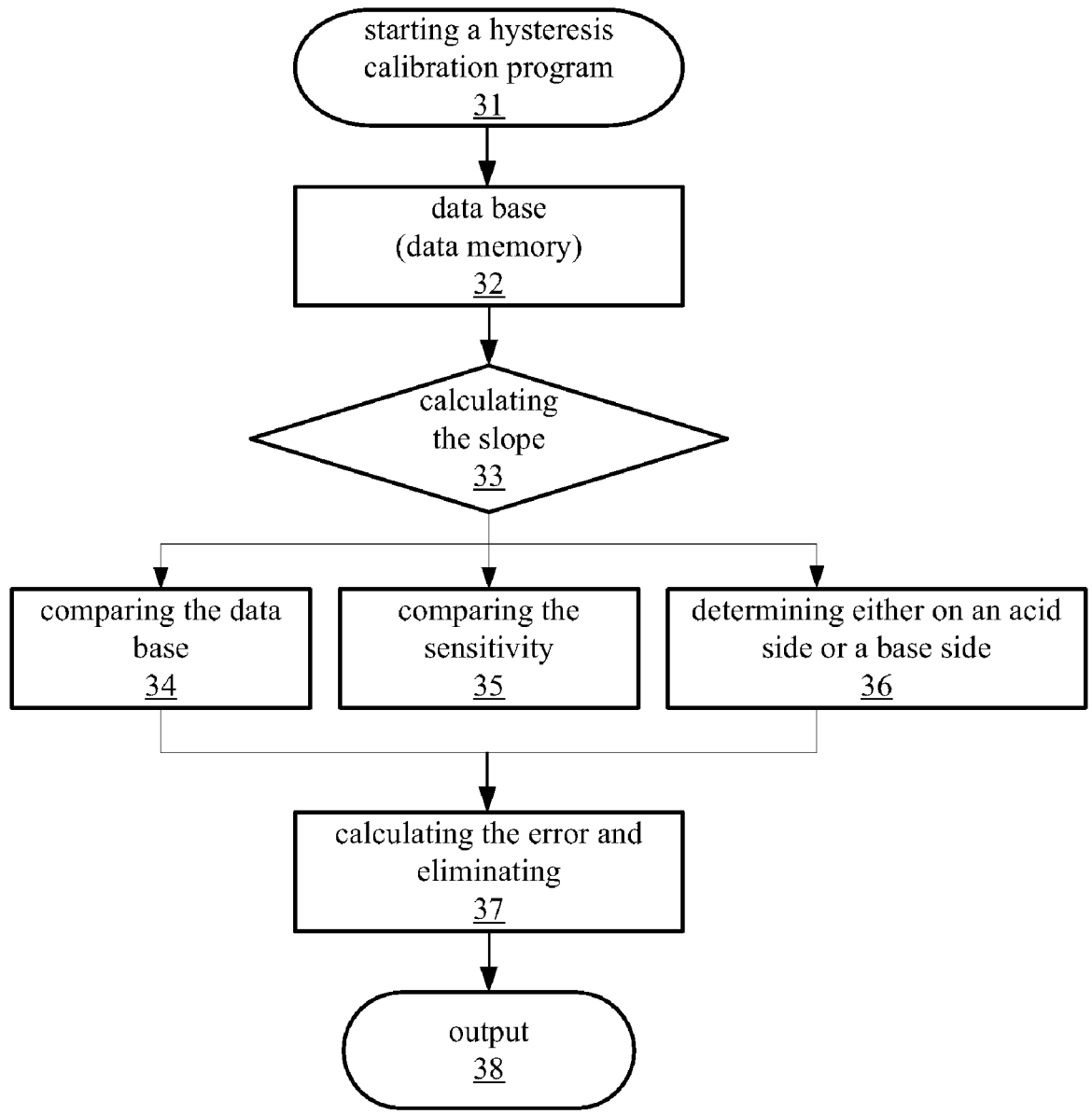
FIG. 8 shows a program flow chart of the hysteresis calibration procedure in a preferred example according to the present invention.

FIG. 8 shows a program flow chart of the hysteresis calibration procedure in a preferred example according to the present invention, comprising the following:

starting a hysteresis calibration program 31 (using a PIC18F452 microprocessor as a processing core);

recording every measurement value in a data memory as a data base 32;

calculating the slope 33 for every measurement;

comparing the data base 34 with the sensitivity 35 calculated from the two-point calibration and determining the process is either on an acid side or a base side 36;

calculating the difference (hysteresis quantity) and eliminating the hysteresis quantity 37;

outputting the result 38 from the hysteresis calibration.

Figure 9:
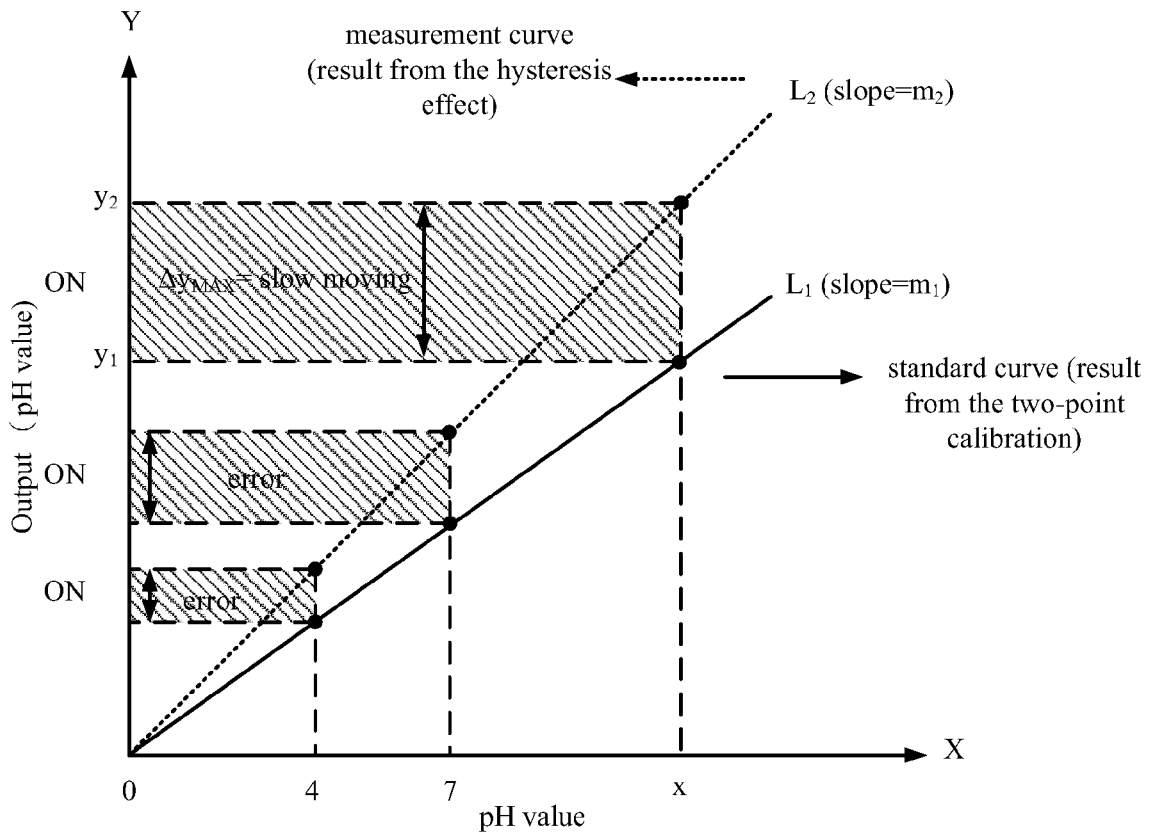
FIG. 9 is a schematic diagram illustrating the drift calibration principle in a preferred example according to the present invention.

FIG. 9 is a schematic diagram illustrating the drift calibration principle in a preferred example according to the present invention, shown in the following:

L1: standard curve (result from the two-point calibration)

$$y = ax + b$$

$$m_1 = \frac{y_1}{x}$$

L2: measurement curve (result from the hysteresis effect)

$$y = cx + d$$

$$m_2 = \frac{y_2}{x}$$

Figure 10:
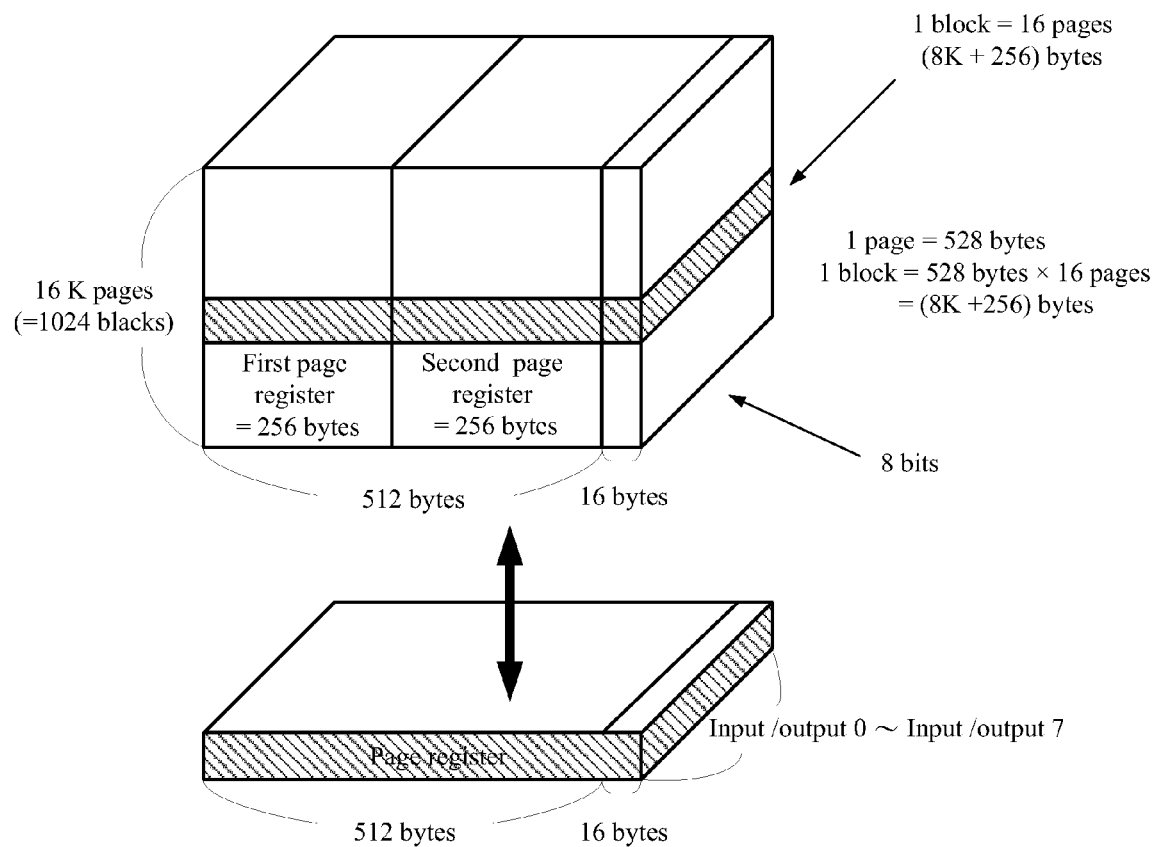
FIG. 10 is a structure diagram of the compact flash card in a preferred example according to the present invention.

If $m_1 \ne m_2$, $Error = y_2 - y_1 = \Delta y = Hysteresis \rightarrow Hysteresis =$ $(m_2 - m_1) \times x \rightarrow Output' = Output - Hysteresis$ FIG. 10 is a structure diagram of the compact flash card in a preferred example according to the present invention.

A compact flash card is organized as the following:

memory cell array: 528×16K×8 bytes;

register: 528×8 bytes;

page: 528 bytes;

block: 8K+256 bytes;

a block comprises 16 pages and a page comprises 528 bytes.

In order to be compatible with the conventional disk drive configuration, byte 0~511 (first 512 bytes) is treated as one sector and byte 512~528 (last 16 bytes) is treated as a spare region.

Figure 11:
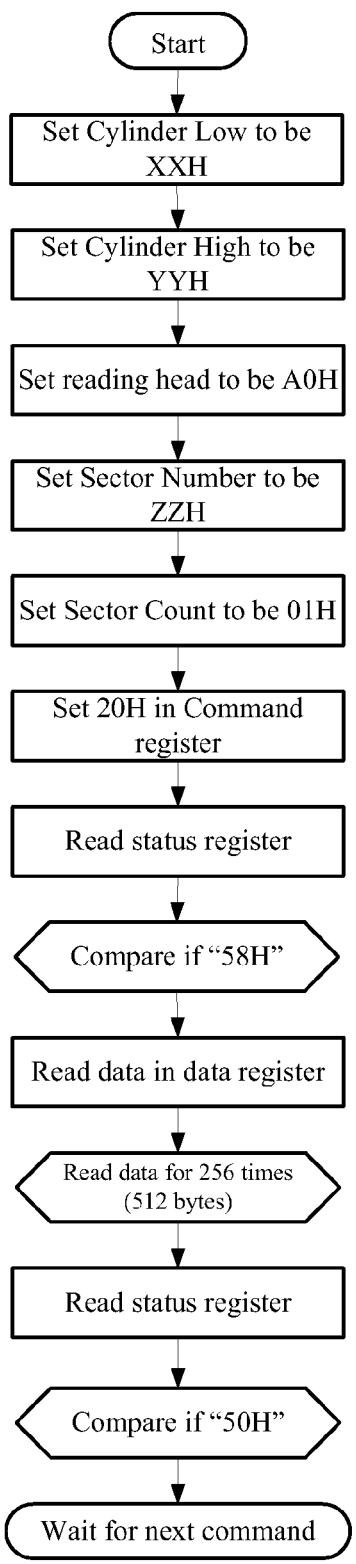
FIG. 11 is a program flow chart of the compact flash card in a preferred example according to the present invention.
Figure 11:
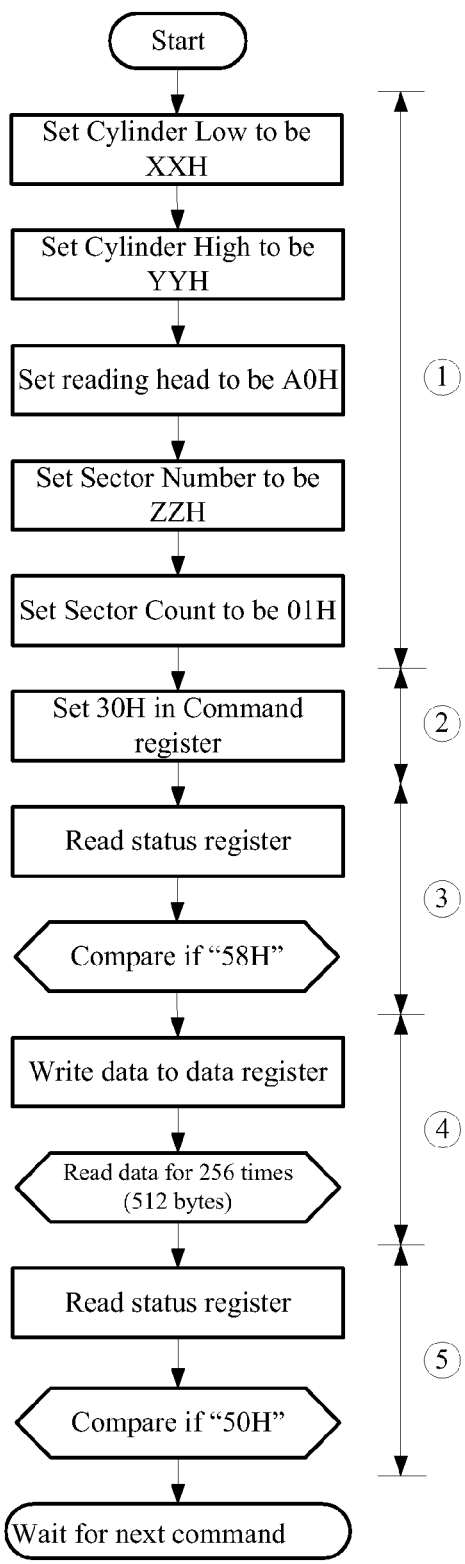

FIG. 11 is a program flow chart of the compact flash card in a preferred example according to the present invention, shown in the following.

Procedure for reading the sector:

Step 1: setting CHS parameters in Cylinder Low, Cylinder High, Sector Number, and Sector Count registers in which data in the Sector Count register is set to be 01H in order to request 256 times of data reading and the total capacity is one sector;

Step 2: sending a reading command to the command register in which the command code is 20H and the address of the register to write in is 07H;

Step 3: reading the parameters in the status register in which the memory card is ready for data transmission (DRQ=1) between the CPU and the memory card if BUSY=0, RDY=1, DSC=1, and DRQ=1 in the status register, i.e. 58H status code;

Step 4: reading the parameters at the memory address in the data register and writing in the data buffer for 256 times in which the memory address pointer in the data buffer increases progressively after each writing in; and, Step 5: confirming if the memory card returns to the ready status and the data request status is finished after data reading is complete, that is, the parameters BUSY=0, RDY=1, DSC=1, and DRQ=0 in the status register, i.e. 50H status code, representing the memory card is ready for next command input.

The procedure for writing into the sector is similar to that for reading except that the command code is 30H in the step 2 for writing instead of 20H for reading. According to the above described reading and writing procedure flow, data access can be complete.

Figure 12:
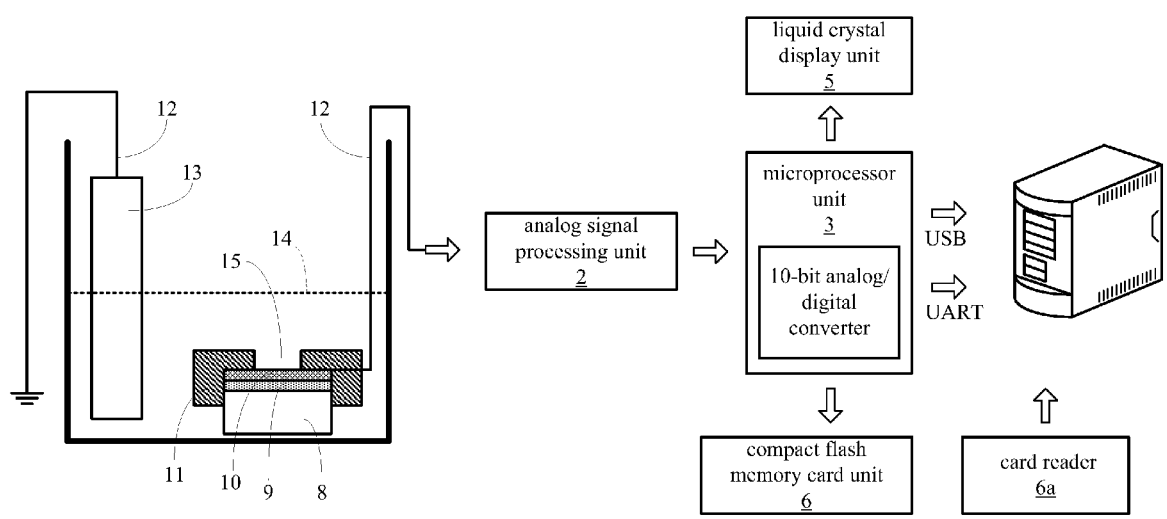
FIG. 12 is a structural schematic diagram illustrating a multi-functional pH meter in a preferred example according to the present invention.

FIG. 12 is a structural schematic diagram illustrating a multi-functional pH meter integrating the preferred examples shown in FIGS. 1 and 2 according to the present invention. The multi-functional pH meter is fabricated by integrating a separate structure extended gate ion selective field effect transistor and embedded system technique. The sensor unit 1, which is a transducer for measuring an unknown solution, comprises a substrate 8; an indium tin oxide film 9 formed on the substrate 8; a tin dioxide film 10 formed on the indium tin oxide film 9 and connected to a conductive wire 12. A package material 11 covers the tin dioxide film 10, the indium tin oxide film 9, and a portion of the substrate 8 and has a sensing window 15 to expose a portion of the tin dioxide film 10. An electrode 13 for measuring the reaction potential of the sensor unit placed in an unknown solution 14 is connected to the conductive wire 12. An analog signal processing unit/circuit 2 is for processing the sensing signal. A microprocessor unit 3 is used for converting analog/digital signals and processing digital signals, comprising a drift-hysteresis calibration processing unit 4, a liquid crystal display unit 5 for displaying the pH value measurement result immediately, a compact flash memory card unit 6 for storing the pH value measurement result, and a data transmission unit 7 for transmitting the pH value to a computer via universal serial bus (USB) and universal asynchronous receiver/transmitter (UART) interfaces, in the firmware portions. The stored pH value measurement result is transmitted to a personal computer or a laptop computer via a card reader 6a.

Figure 13:
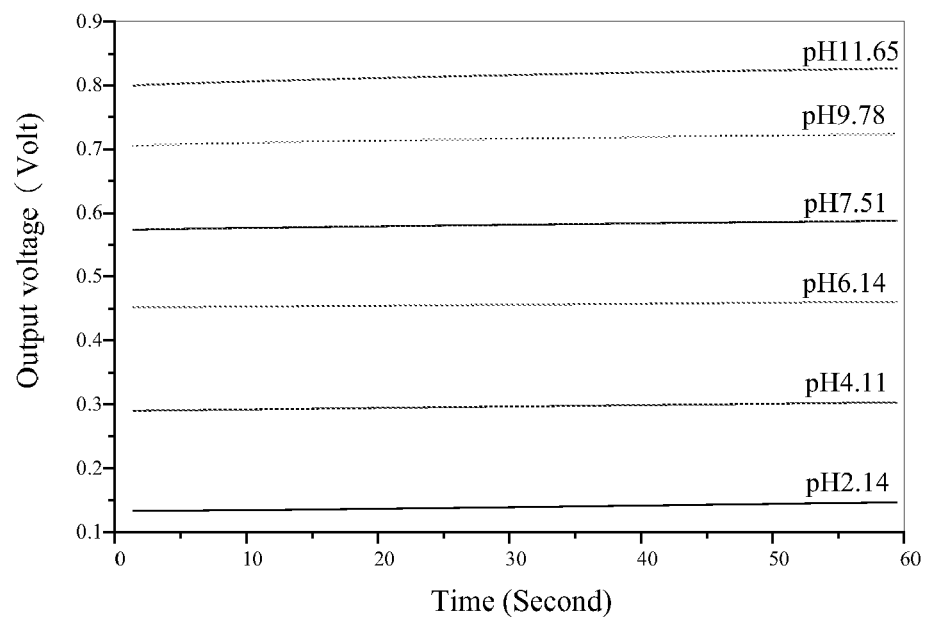
FIG. 13 is a steady-state voltage output diagram of the multi-functional pH meter in a preferred example according to the present invention.

FIG. 13 is a steady-state voltage output diagram of the multi-functional pH meter in a preferred example according to the present invention. According to the experimental result, the output voltage changes along with time but can be maintained in the range between 0V and 1V.

Figure 14:
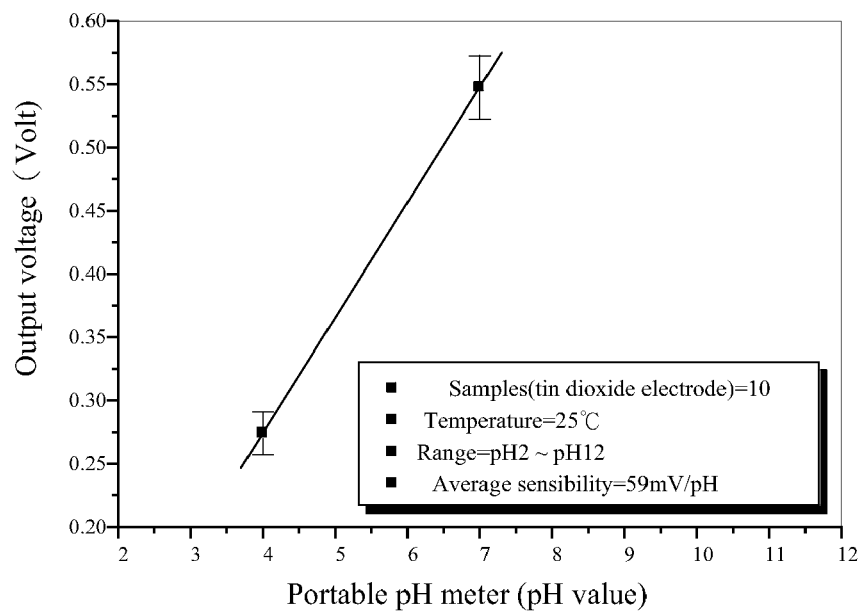
FIG. 14 is a two-point calibration curve of the multi-functional pH meter in a preferred example according to the present invention.

FIG. 14 is a two-point calibration curve of the multi-functional pH meter in a preferred example according to the present invention. According to the experimental result, the device according to the present invention has the two-point calibration result in a fixed range for different sensor units and the average sensitivity of the sensors is 59 mV/pH.

Figure 15:
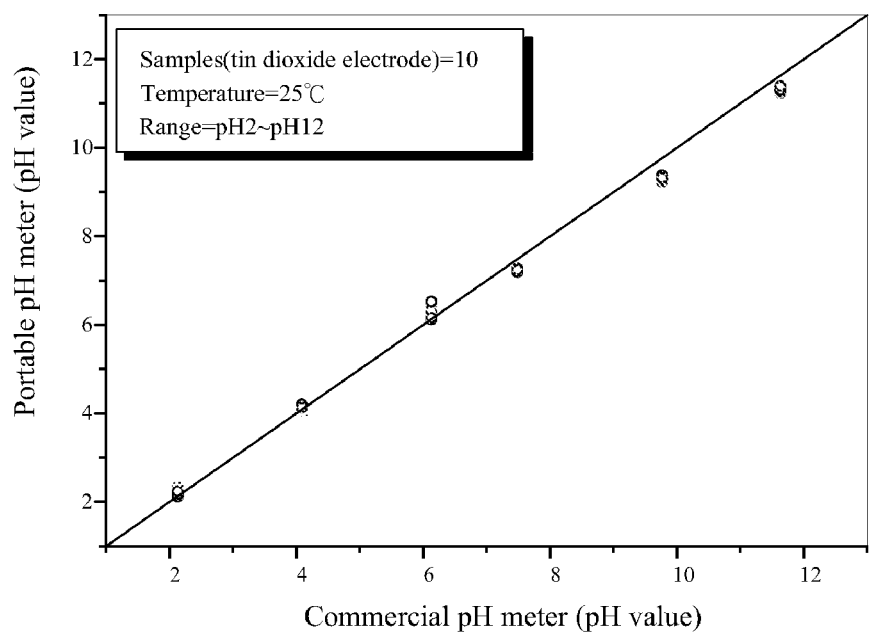
FIG. 15 is a linear distribution curve of the multi-functional pH meter in a preferred example according to the present invention; and, FIG. 16 is a linear calibration curve of the multi-functional pH meter in a preferred example according to the present invention.

FIG. 15 is a linear distribution curve of the multi-functional pH meter in a preferred example according to the present invention. According to the experimental result, the characteristic of the sensor and the stability of the system are excellent.

Figure 16:
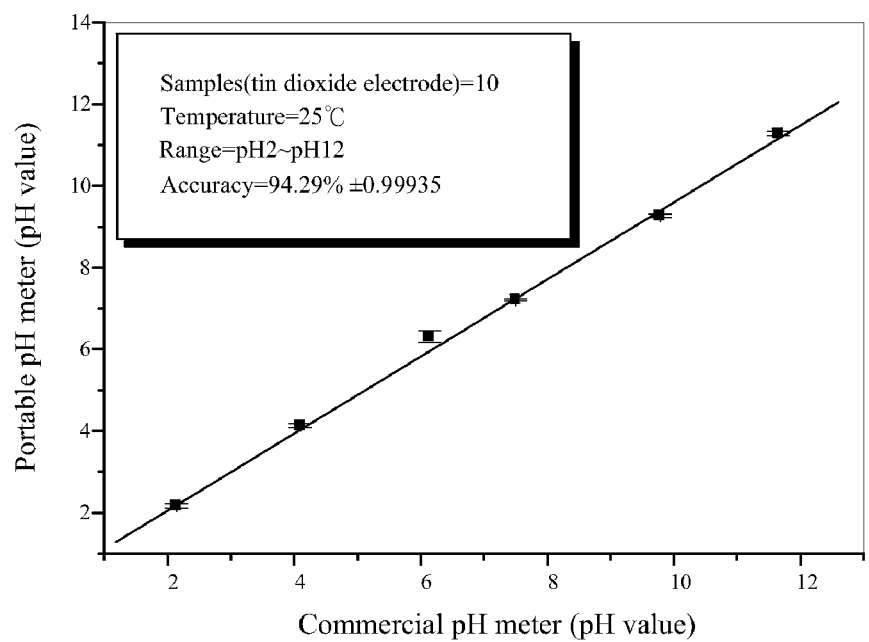

FIG. 16 is a linear calibration curve of the multi-functional pH meter in a preferred example according to the present invention. According to the experimental result, the multi-functional pH meter according to the present invention has 94.29% accuracy, compared to the commercial pH meter.

Table 1 shows measurement results in various buffer solutions (from pH 2 to pH 12) by the multi-functional pH meter in a preferred example according to the present invention. Compared to the commercial pH meter, the multi-functional pH meter according to the present invention has very small errors, in the range between 2% to 4%. It has excellent functionality and potential in commercialization.

Table 2 shows the specification of the multi-functional pH meter in a preferred example according to the present invention.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A multi-functional pH meter, comprising:
   a sensor unit comprising a substrate, an indium tin oxide film on said substrate, a sensing film on said indium tin oxide film and connecting to a conductive wire, an electrode, and a package material covering said sensing film, said indium tin oxide film, and a portion of said substrate and exposing the sensing film via a sensing window;
   an analog signal processing unit for processing analog signals from said sensing unit via said conductive wire;
   a microprocessor unit for receiving the signals from said analog signal processing unit and generating a pH value of a solution being detected;
   a liquid crystal display unit for displaying the pH value;
   a compact flash card unit for storing the pH value;
   a data transmission unit for transmitting the pH value to a computer via Universal Serial Bus (USB) and Universal Asynchronous Receiver/Transmitter (UART) interfaces;
   an amplifier used as a front-end processing circuit for a sensing signal to increase the signal-to-noise ratio of said sensing signal;
   a low pass filter for filtering low frequency noises and suppressing the interference of the 60 Hz AC mains frequency to said sensing signal; and
   a level adjusting circuit for adjusting the potential level of the processed sensing signal to fit the input range and specification of a analog/digital converter.

2. The meter according to claim 1, wherein said sensing film comprises a tin dioxide film.

3. The meter according to claim 2, wherein said tin dioxide film is deposited on said indium tin oxide film and said substrate by a RF (radio frequency) sputtering method.

4. The meter according to claim 3, wherein the thickness of said tin dioxide film is about 2000 Å.

5. The meter according to claim 1, wherein said substrate comprises a ceramic substrate.

6. The meter according to claim 1, wherein said substrate comprises a glass substrate.

7. The meter according to claim 1, wherein said conductive wire comprises a silver wire.

8. The meter according to claim 7, wherein said silver wire is adhered to said sensing film via silver paste.

9. The meter according to claim 1, wherein said package material comprises epoxy resin.

10. The meter according to claim 1, wherein said electrode comprises a silver/silver chloride glass electrode.

11. The meter according to claim 1, wherein said sensing window has an area of 3 mm×3 mm on said package material.

12. The meter according to claim 1, wherein said microprocessor unit comprises:
    a firmware of analog/digital converting procedure for controlling 10-bit analog/digital converter built in said microprocessor unit, comprising controls of sampling rate, channel selection, and reference potential;
    a firmware of two-point calibration procedure for completing said two-point calibration procedure; and,
    a firmware of drift and hysteresis calibration procedure for calibrating drift phenomena and hysteresis effect.

13. The meter according to claim 1, wherein the transmission interface of said data transmission unit comprises Universal Serial Bus (USB) and Universal Asynchronous Receiver/Transmitter (UART) interfaces.

14. The meter according to claim 1, wherein said microprocessor unit receives the signals from said analog signal processing unit and thereby calculates the procedure of processing the pH value, comprising:
    carrying out analog signal quantization by a analog/digital converter;
    performing a two-point calibration procedure and calculating the pH value;
    performing a drift and hysteresis calibration procedure for the pH value;
    immediately displaying the pH value on said liquid crystal display unit;
    saving the pH value in said compact flash card unit;
    transmitting the pH value to a computer.

15. The meter according to claim 14, wherein the procedure of processing the pH value calculated by said microprocessor unit further comprises: reading out the pH value from said compact flash card unit by a card reader and into a computer.

16. The meter according to claim 14, wherein said drift calibration procedure comprises:
    starting a drift program;
    recording every measurement value in a data memory as a data base;
    comparing the data base with the reference pH value (pH ref) and calculating the difference for every measurement;
    determining if the difference is caused by drift phenomena or variation in the tested solution and carrying out calibration; and
    outputting the result from the calibration procedure.

17. The meter according to claim 14, wherein said hysteresis calibration procedure comprises:
    starting a hysteresis calibration program;
    recording every measurement value in a data memory as a data base;
    calculating the slope for every measurement;
    comparing the data base with the sensitivity calculated from the two-point calibration and determining the process is either on an acid side or a base side;
    calculating the difference (hysteresis quantity) and eliminating the hysteresis quantity;
    outputting the result from the hysteresis calibration.

* * * * *